United States Patent
Einziger

(10) Patent No.: US 7,205,000 B2
(45) Date of Patent: Apr. 17, 2007

(54) SODIUM BICARBONATE/SODIUM CHLORIDE MICRONIZED SLURRY

(75) Inventor: Mark D. Einziger, Manalapan, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 141 days.

(21) Appl. No.: 10/116,766

(22) Filed: Apr. 4, 2002

(65) Prior Publication Data

US 2003/0190373 A1    Oct. 9, 2003

(51) Int. Cl.
*A61K 33/00*    (2006.01)
*A61K 33/14*    (2006.01)

(52) U.S. Cl. .................. 424/600; 424/680; 424/717

(58) Field of Classification Search ............... 424/400, 424/401, 49–58, 600, 680, 717; 423/421
See application file for complete search history.

(56) References Cited

U.S. PATENT DOCUMENTS

| | | | | |
|---|---|---|---|---|
| 4,024,237 A | * | 5/1977 | Eichel et al. ................ | 424/49 |
| 4,129,527 A | | 12/1978 | Clark et al. ................ | 252/547 |
| 4,664,891 A | * | 5/1987 | Cosentino et al. .......... | 422/269 |
| 4,897,207 A | * | 1/1990 | Greene ...................... | 252/2 |
| 5,004,596 A | * | 4/1991 | Cocherell et al. ........... | 424/52 |
| 5,038,396 A | * | 8/1991 | Gjerlov ...................... | 424/737 |
| 5,071,558 A | * | 12/1991 | Itoh ........................... | 210/542 |
| 5,294,427 A | * | 3/1994 | Sasaki et al. .............. | 423/415.2 |
| 5,411,750 A | | 5/1995 | Lajoie et al. ................ | 424/717 |
| 5,424,077 A | | 6/1995 | Lajoie ........................ | 424/641 |
| 5,466,470 A | | 11/1995 | Lajoie ........................ | 424/641 |
| 5,518,727 A | | 5/1996 | Lajoie et al. ................ | 424/400 |
| 5,540,842 A | * | 7/1996 | Aoyama et al. ............. | 210/647 |
| 5,645,840 A | | 7/1997 | Lajoie et al. ................ | 424/400 |
| 5,855,871 A | * | 1/1999 | Masters et al. .............. | 424/49 |
| 5,965,189 A | * | 10/1999 | Stevens et al. ............. | 426/549 |
| 6,015,547 A | | 1/2000 | Yam ........................... | 424/49 |

FOREIGN PATENT DOCUMENTS

JP    408099847 A  *  4/1996

OTHER PUBLICATIONS

U.S. Appl. No. 09/814,401, filed Mar. 22, 2001, Inventor:Einziger et al; entitled Micron Sized Bicarbonate Particles and Slurry Containing the Same.

* cited by examiner

*Primary Examiner*—Sreeni Padmanabhan
*Assistant Examiner*—Marina Lamm
(74) *Attorney, Agent, or Firm*—Allen R. Kipnes; Stephen B. Shear

(57) ABSTRACT

A slurry comprising (a) sodium bicarbonate, (b) sodium chloride, and (c) water, in a weight ratio of (a)/(b) of about 2.5:1 to about 3.5:1, wherein upon further dilution of said slurry with additional water, the amount of sodium bicarbonate and sodium chloride which dissolves into said additional water is in the same ratio as said of (a)/(b) in said slurry before said additional dilution.

6 Claims, No Drawings

SODIUM BICARBONATE/SODIUM CHLORIDE MICRONIZED SLURRY

CROSS-REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

The present invention relates to the field of slurries of sodium bicarbonate. It further relates to slurries of sodium chloride. It also relates to micronized slurries of these materials and to the use of the two materials in a fixed ratio in a single slurry. The present invention further relates to the use of such slurries in a variety of formulations in which both sodium bicarbonate and sodium chloride are present, but especially to the use of the slurry in hemo and peritoneal dialysis applications.

BACKGROUND OF THE INVENTION

Sodium bicarbonate has become a substantial component of hemo and peritoneal dialysate solutions. In many situations, these dialysate solutions are prepared and transported in ready to use form to the site of use, most typically a dialysis clinic. This has the drawback that large volumes of water need to be transported, thereby increasing the cost of transportation significantly as well as requiring large areas for storage of sufficient solution for use. In an effort to reduce the large volumes of water contributing to cost and space and sterility issues, dry powder forms of the dialysis components or dry mixtures of the needed components have been tried. The difficulty here is that the components must be diluted, typically batch style, which increase preparation time at the clinic site and require large volume mixing tanks for each dialysis unit, thereby restricting the available floor space for dialysis units themselves and thereby limiting the number of dialysis patients that can be treated in a given dialysis clinic to less than would otherwise be needed. As such, efforts have been underway to utilize in line cartridges of the dialysis components for dissolution to the appropriate concentrations with locally supplied reverse osmosis water. Such units have typically used cartridges which contained dry powder. Where dry powders have been used, the problems associated therewith include those such as inconsistent concentrations flowing out of the cartridge, which require concentration monitoring and adjustment of various other dilution controls to result in the appropriate concentrations in the final dialysate.

In addressing the above concerns, the instant inventor and other coworkers have proposed a micronized slurry of sodium bicarbonate for use in such cartridges. The micronized slurry eliminates the large water tank and transportation issues of the solutions, and overcomes the dissolution inconsistency of the dry powder cartridges. Such slurries are set forth in detail in copending application Ser. No. 09/814,401, filed Mar. 22, 2001, entitled MICRON SIZED BICARBONATE PARTICLES AND SLURRYS CONTAINING THE SAME, the full text of which is incorporated herein by reference.

In preparing the full dialysate solution, there are generally two pre-solutions prepared which are mixed just prior to exposing the patient or patient's blood to the full dialysate. One of these pre-solutions contains sodium bicarbonate and sodium chloride in a weight ratio of sodium bicarbonate to sodium chloride of about 3:1. When dry powder bulk material (for bulk dilution before beginning the dialysis treatment) the sodium bicarbonate and sodium chloride have been typically been pre-blended in the appropriate ratio and the clinic staff assure completed dissolution of the materials before they are used.

The saturation solubility of sodium bicarbonate in water is generally known to decrease with temperature. For example, sodium bicarbonate saturation concentrations in water are about 10% weight/volume at 25° C., 8.5% at 22° C., and about 7% at 10° C. The saturation solubility of sodium chloride in water is about 36.1% weight/volume at 25° C., 35.7% at 22° C., and about 35.7% at 10° C. Owing to the solubility differences between these two components, especially in the greater solubility of sodium chloride, one would not have expected that one could combine both sodium chloride and sodium bicarbonate in a single slurry and achieve consistent effluent concentration upon dissolution of the slurry over the effective lifetime of the slurry dissolution time where the sodium bicarbonate concentration would exceed the sodium chloride concentration.

OBJECTS OF THE INVENTION

Therefore, an object of the invention is to provide a slurry of a mixture of sodium bicarbonate and sodium chloride which will, upon partial dissolution, result in a solution phase which is consistently reflective of the concentrations of these materials in the undiluted slurry.

Another object of the invention is to provide a slurry of a mixture of sodium bicarbonate and sodium chloride which will, upon partial dissolution, result in a solution phase having a sodium bicarbonate:sodium chloride weight ratio of approximately 3:1.

Still another object of the invention is to provide a cartridge for dispensing a fixed ratio of sodium bicarbonate: sodium chloride, when the cartridge contains the same weight ratio of sodium bicarbonate to sodium chloride in a slurry form.

Yet another object of the invention is to provide a hemo, peritoneal, or kidney dialysis unit cartridge capable of delivering therefrom, a consistent fixed weight ratio of sodium bicarbonate:sodium chloride.

An even further object of the invention is to provide an improved method of administering a dialysis solution by incorporating a dialysis cartridge capable of delivering therefrom a consistent fixed weight ratio of sodium bicarbonate:sodium chloride into the dialysis unit.

Still other objects of the invention will be appreciated by those of ordinary skill in the art.

BRIEF SUMMARY OF THE INVENTION

These and other objects of the invention can be surprisingly achieved by comicronizing sodium bicarbonate and sodium chloride in a wet milling process to result in a slurry of a weight ratio of sodium bicarbonate:sodium chloride of about 3:1, with a total sodium bicarbonate and sodium chloride content of about 70% w/w. The sodium bicarbonate particles which result have median particle sizes (number count basis) of from about 0.2 to about 50.0 μm with the particles having a surface area of from about 120 to about 140 m²/g. The sodium chloride particles have median particle sizes (number count basis) of from about 2 to about 50 µm.

BRIEF DESCRIPTION OF THE SEVERAL VIEWS OF THE DRAWING

Not Applicable

DETAILED DESCRIPTION OF THE INVENTION

The present invention provides a stable, flowable slurry comprising, preferably consisting essentially of, and more preferably consisting essentially of sodium bicarbonate and sodium chloride particles in an aqueous slurry, in a weight ratio of about 2.5:12 to about 3.5:1, preferably about 2.75:1 to about 3.25:1, more preferably about 2.9:1 to about 3.1:1, most preferably about 3:1.

The sodium bicarbonate particles have a median particle size of from about 0.2 to about 50.0 µm. Generally, not more than about 0.1% of the sodium bicarbonate particles in the slurry exceed 50.0 µm. Preferably, the sodium bicarbonate particles in the slurry have a average particle size of about 0.2 µm, to 25 µm, more preferably about 0.21 µm to about 15 µm, still more preferably about 0.4 µm to about 0.7 µm. Preferably not more than 2% of the sodium bicarbonate particles in the slurry exceed about 5 µm. Throughout this specification, the use of the term "median" with respect to particle size is intended to mean that about 50% of the particles are smaller than and about 50% of the particles are greater than the specific size (when one does not include the particles which are at the stated particle size).

The sodium bicarbonate particles in the slurry have a surface area of about 120 to about 140 m²/g, preferably about 127 to about 130 m²/g. The loose bulk density of the slurry is from about 1.4 to about 1.6 g/ml, preferably about 1.49 g/ml.

The slurries of the invention are stable for months and do not require the presence of a suspending aid. In fact, in the dialysis utility, the use of a suspending aid would be contraindicated. Hence, the present invention slurries preferably are free of any suspending aid, or other dialysate non-compatible component.

The slurry of the present invention, upon contact with water achieves rapid dissolution of both the sodium bicarbonate and the sodium chloride, in the same ratio as present in the slurry despite the widely different solubilities of the components of the slurry. This rapid dissolution is achieved at low temperatures, typically of about 5° C. to about 20° C., preferably about 10° C. to about 20° C. and reaches the same concentration of the components as would be achieved at about room temperature (generally about 22.5° C.) This corresponds to about 8.5% weight/volume of sodium bicarbonate and about 2.83% of sodium chloride. Thus the slurry of the instant invention can be diluted at lower temperatures and only the volume actually being used for patient treatment, if any, needs to be warmed at all, making the use of the instant slurry more economical.

The slurry of the invention is prepared generally as follows. Typical commercially available USP Grade granular sodium bicarbonate and sodium chloride granules (about 100 µm to 1000 µm) are introduced, along with water, into a running wet media milling processing mill. Preferably the starting sodium bicarbonate is Church & Dwight Grade 1 or Grade 4 sodium bicarbonate, having an average particle size of about 45 µm to about 175 µm. The sodium chloride starting material is preferably Morton granular sodium chloride having a particle size range of about 200 µm to about 1000 µm with an average particle size of about 400 µm to about 600 µm. The amount of sodium bicarbonate and sodium chloride used are in the ratio of about 2.8:1 to about 3.0:1 and in concentrations with the water component so that the resulting slurry is preferably 70% solids. This charge is then processed in the mill for about 8 to about 18 minutes, preferably about 10 minutes at about 2,000 to about 2,500 rotations per minute, preferably about 2,200 rotations per minute. The contents of the mill are then emptied.

The above wet milling occurs in the presence of an inert grinding medium, such as yttrium stabilized zirconia beads, stainless steel beads, among others known in the grinding arts. Preferably the grinding media is yttrium stabilized grinding beads of about 2 mm size.

The resulting slurry contains the combined weight of sodium bicarbonate and sodium chloride in a range of from about 50% to about 80%, preferably about 60% to about 75%, more preferably about 65% to about 72%, and most preferably about 70% of the total slurry weight. Water makes up about 20% to about 50%, preferably about 25% to about 40%, more preferably about 28% to about 35%, and most preferably about 30% of the weight of the slurry. Most preferably, the slurry is made up of sodium bicarbonate, sodium chloride, and water with no other components. Nonetheless, when the end use is dialysis, where suitable, dialysate compatible components which do not interact with the sodium bicarbonate and do not interact with the sodium chloride can be added in small amounts. When the end-use is other than dialysate application, other final formulation components may be present in the slurry itself so long as they do not adversely affect the slurry formed between the bicarbonate/chloride/water system.

Particle sizes are determined using a Pacific Scientific Instruments, Model 8000A/3000A/MC05 analyzer.

The viscosity of the slurries of the invention are less than about 1,000 cP as measured with a Brookfield Viscometer RVT unit operated at 50 rpm with a No. 2 spindle at about 22° C. directly on the slurry without further dilution.

The slurry of the instant invention may be used in any number of applications, as long as the amount of sodium chloride and water which accompanies the sodium bicarbonate is acceptable for the end use application. This is particularly so for industrial manufacturing of compositions having each of the components of the slurry present. Nonetheless, the most advantageous use of the invention slurry is in the are of dialysis treatments. While the slurry may be diluted in bulk tanks for use, its primary advantage is for use in in-line cartridges in dialysis units. In this preferred usage, water is introduced into the cartridge diluting the slurry. Outflow of the solution is saturated with sodium bicarbonate and contains the sodium chloride in the range of about 1:2.5 to about 1:3.5 relative to the sodium bicarbonate. The effluent from the cartridge is then directed to further dilutions and contact with other dialysate materials for introduction into the dialysis treatment. As long as the cartridge contains slurry, the effluent from the cartridge contains substantially a constant concentration of sodium bicarbonate and sodium chloride.

Cartridges in which the slurry is contained are generally known in the art or are prepared as indicated in copending application Ser. No. 09/814,401, filed Mar. 22, 2001, entitled MICRON SIZED BICARBONATE PARTICLES AND SLURRYS CONTAINING THE SAME. Other cartridge variations will be apparent and within the abilities of those of ordinary skill in the art.

The present invention will be more fully appreciated from the following examples, which merely exemplify but do not limit the scope of the invention.

EXAMPLES

Example 1

This Example illustrates the preparation of the micron-sized particels of the invention by a wet mill process of the invention and the resulting stable, flowable slurry. The slurry is useable in any application which calls for the use of sodium bicarbonate and which is tolerant of the sodium chloride being present.

A water source (sterilized if the end use so requires, but otherwise sterilization not necessarily required) is blended with a mixture of sodium bicarbonate Church & Dwight Grade 1 and sodium chloride in the weight ratio set forth in the Table below. Example Ic is repeated using Church and Dwight sodium bicarbonate Grade 4 and is reported as Example If. Example Ig is a repeat of Example Ib with a slightly different ratio of sodium bicarbonate to sodium chloride. The particle sizes for the sodium bicarbonate and sodium chloride starting materials are set forth below:

|  | (Tyler US Mesh) Sieve Size | Minimum Particles Remaining on Sieve | Maximum Particles Remaining on Sieve |
|---|---|---|---|
| Church & Dwight Sodium Bicarbonate |  |  |  |
| Grade 1 | 100 | 0% | 0.9% |
| Grade 1 | 200 | 20% | 45% |
| Grade 1 | 325 | 80% | 100% |
| Grade 4 | 80 | 0% | Trace |
| Grade 4 | 100 | 0% | 2% |
| Grade 4 | 200 | 80% | 100% |
| Grade 4 | 325 | 93% | 100% |

| Morton Salt | Parts $NaHCO_3$ | Parts NaCl |
|---|---|---|
| Example Ia | 2.7 | 1.0 |
| Example Ib | 2.8 | 1.0 |
| Example Ic | 2.9 | 1.0 |
| Example Id | 3.0 | 1.0 |
| Example Ie | 3.1 | 1.0 |
| Example If | 2.9 | 1.0 |
| Example Ig | 2.83 | 1.0 |

To each of the above sufficient water is added to the sodium bicarbonate/sodium chloride mixture so that the total sodium bicarbonate/sodium chloride concentration is as set forth below (in weight %):

|  | 1 | 2 | 3 | 4 |
|---|---|---|---|---|
| Example Ia | 50 | 60 | 70 | 80 |
| Example Ib | 50 | 60 | 70 | 80 |
| Example Ic | 50 | 60 | 70 | 80 |
| Example Id | 50 | 60 | 70 | 80 |
| Example Ie | 50 | 60 | 70 | 80 |
| Example If | 50 | 60 | 70 | 80 |
| Example Ig | 50 | 60 | 70 | 80 |

In each of examples Ia1–Ia4, Ib1–Ib4, Ic1–Ic4, Id1–Id4, Ie1–Ie4, If1–If4 and Ig1–Ig4 the respective amounts of the sodium bicarbonate, sodium chloride, and water, are placed in a running Eiger self contained horizontal feed mill. The media utilized is 45% by weight of 0.4 mm Yttrium stabilized zirconia grinding beads. The process is conducted at a temperature of about 10° C., and the wet milling continues for a period of fifteen minutes at a speed of 3,200 rotations per minute. The slurry is then emptied from the bead mill.

Each of the resulting slurries has a flowable consistency. Upon standing for thirty minutes, the slurries retain their flowable consistency. The resulting sodium bicarbonate particles have a median size of about 0.4 µm to about 0.7 µm and the sodium chloride has a median particle size of about 2µm to about 50 µm.

Comparative Example A is prepared as in Example Ig3 except that a dry mill is used without the water. Comparative Examples B–D are prepared using air milled particles, but otherwise the procedure for the preparation of Example Ig3 is followed.

Comparative Example E is prepared in accordance with Example Ig3 except that a ball mill is used instead of the bead mill. The milling time is greater than 72 hours with losses of greater than 50%. Comparative Example F is prepared in accordance with Example Ig3 except that homogenization is also included.

The results are summarized in the Table below:

| Example | Median Particle Size | Consistency | Consistency after 30 minutes |
|---|---|---|---|
| Ia1–Ie4 | 0.4–0.7 µm | flowable slurry | flowable |
| Compar. A | >15 | no slurry -settles Within 2 min. | N/A |
| Compar. B | 15 µm | wet cement | hard packed |
| Compar. C | 10 µm | wet cement | hard packed |
| Compar. D | 5 µm | wet cement | hard packed |
| Compar. E | — | paste | N/A |
| Compar. F | — | hard packed | N/A |

Example 2

This illustrates the use of the slurries of the invention in a dialysis application. The slurry of Example Ig3 is packaged and delivered to a dialysis unit user. The package may be emptied into a tank with other dialysis components or used in automated mixing equipment. The slurry readily dissolves into the dialysis solution and is ready for use with a dialysis patient.

Example 3

This illustrates an oral care product, specifically a toothpaste, toothgel, or tooth polish. In these applications, the sodium bicarbonate/sodium chloride slurry of Example Ig3 is used in amounts from about 1.43% to about 98%. The final product need not still have a slurry in it, but the use of the slurry allows for incorporation of significant amounts of sodium bicarbonate without concern for getting the bicarbonate into solution. If the final product retains some of the bicarbonate as not dissolved, the slurry permits for the rapid dissolution of the bicarbonate upon contact with additional water when the product is used.

Humectants may also be present in amounts of from about 5% to about 50%, preferably from about 10% to about 40%. Exemplary humectants include, but are not limited to, glycerin, sorbitol, mannitol, etc. These formulations may also include abrasives over and above any solid particles remaining from the slurry used. Such additional abrasives may comprise up to about 50% of the formulation. Exemplary, non-limiting abrasives include silica, aluminum oxide, talc, calcium carbonate, etc. When calcium carbonate is used, the carbonate portion of the calcium carbonate is not to be considered in the calculations as part of the bicarbonate.

Surfactants may also be present in amounts of about 0.1% to about 10%, preferably about 0.3% to about 3% of the formulation, and may be selected from anionic, cationic, nonionic, and amphoteric surfactants. Typical of such surfactants include, but are not limited to, sodium lauryl sulfate, sodium lauroyl sarcosinate, amine oxides, betaines, etc.

A thickener or viscosity booster may also be included in amounts of up to about 15% of the formulation. Typically used thickeners include carboxymethylcellulose (or its sodium salt), magnesium aluminum silicates, carrageenan gum, alginates, fumed silicas, and hydrated silicas.

Other typical components for formulations of this type include, but are not limited to a cavity control agent (such as sodium fluoride, sodium monofluorophosphate, stannous fluoride, etc.); a tartar control agent (such tetrasodium pyrophosphate, sodium tripolyphosphate, etc.); sensitivity reducing agents (such as potassium salts, etc., especially potassium nitrate); peroxides (or entities which result in a peroxide or generate active oxygen such as sodium percarbonate, sodium perborate, urea peroxide, calcium peroxide, etc.); sweeteners (such as saccharine, acesulfame, aspartame, sucralose, sugar alcohols, etc.); flavors; dyes; antibacterial agents (such as CPC, triclosan, zinc salts etc); etc.

Example 4

This illustrates the use of the invention slurry in a skin cleanser. The sodium bicarbonate/sodium chloride slurry of the invention Example Ig3 is typically used in this application in amounts of at least 1.43%. In addition, the formulation contains about 5% to about 305 surfactants. The surfactants of choice include, but are not limited to, sodium α-olefin sulfonates, cocamidopropyl betaines, and alkylbenzene sulfonates.

Lathering agent or foam boosters are often present and may be used in amounts of up to about 5% of the formulation. Examples include, but are not limited to, lauramide MEA, sodium lauroylsarcosinate, and sodium cocoylisothionate.

Thickeners or viscosity enhancers may also be present up to about 10% of the formulation. Examples include, but are not limited to, carboxymethylcellulose 9 or its sodium salt), hydroxypropylcellulose, hydroxypropyl guar gum, magnesium aluminum silicate, carageenean gum, etc. Other optional skin cleanser formulation ingredients include, but are not limited to, antimicrobial agents (such as Triclosan), preservatives (such as sodium hydroxymethylglycinate, methylparaben, etc.), skin substantive aids, chelating agents (such as EDTA and its salts), fragrances, dyes, etc.

Example 5

This illustrates the use of the invention slurry in an ostomy deodorant product. In this application, the invention slurry of Example Ig3 is typically used in an amount of at least 1.43% up to about 35.75% of the formulation. Zinc ion is present from a zinc ion source in an amount so that the zinc ion content of the formulation is about 0.01 wt % to about 2 wt % of the formulation. A stabilizing anion (such as citrate) concentration is present in a minimum amount as set forth in U.S Pat. No. 6,015,547 (incorporated herein by reference) so as to prevent the reaction of the zinc ion and the bicarbonate ion and the resulting precipitation of the zinc bicarbonate salts. In addition, the formulations can have solvents such as alcohols (preferably ethyl alcohol), preservatives, fragrances, and dyes as desired.

Example 6

This illustates the use of the present invention slurry in a toilet deodorizer/sanitizer. Products of this nature include liquids which dispense into the toilet tank with each flush. The slurry of the invention Example Ig3 is used in amounts of at least 1.43% of the formulation to about 98% of the formulation. A zinc ion in an amount so that the zinc ion content of the formulation is about 0.01 wt % to about 2 wt % of the formulation. A stabilizing anion (such as citrate) concentration is present in a minimum amount as set forth in U.S Pat. No. 6,015,547 (incorporated herein by reference) so as to prevent the reaction of the zinc ion and the bicarbonate ion and the resulting precipitation of the zinc bicarbonate salts. The other components of formulations of this type are ewell known in the art.

Example 6

This illustrates the use of the invention slurry in a hard surface cleaner. In these products, the slurry of invention Example Ig3 is typically used in amounts of 714 parts by weight per 1,000 parts of cleaner suspension. Typical further cleaner suspension ingredients include, but are not limited to an amine oxide surfactant (typically 12 to 40 parts by weight per 1000 parts by weight of cleaner suspension), a multiple ionic-oxide containing salt (typically 2 to 30 parts by weight per 1000 parts by weight of cleaner suspension), and an alkylaryl sulfonate (typically at least 16.5 parts by weight per 1000 parts by weight of cleaner suspension). Antibacterial agents (such as Triclosan), coloring agents, perfumes, abrasives, and bleaches may also be present in amounts generally recognized in the art.

I claim:

1. A storage stable prepackaged flowable slurry comprising (a) sodium bicarbonate, (b) sodium chloride in a combined amount of from about 50% to about 80% by weight, and (c) water in an amount of about 20% to about 50% by weight, in a weight ratio of (a)/(b) of about 2.5:1 to about 3.5:1, said sodium bicarbonate particles having a median particle size of about 0.2 µm to about 50 µm and a surface area of about 120 m²/g to about 140 m²/g, wherein upon further dilution of said storage stable prepackaged flowable slurry with additional water, the amount of sodium bicarbonate and sodium chloride which dissolves into said additional water is in the same ratio as said weight ratio of (a)/(b) in said slurry before said additional dilution.

2. The slurry of claim 1 wherein said sodium bicarbonate particles have a median particle size of about 0.5 µm to about 1.0 µm.

3. The slurry of claim 1 wherein said sodium chloride has a median particle size of about 2 µm to about 50 µm.

4. The slurry of claim 1 wherein said sodium bicarbonate together with said sodium chloride comprise about 60% to about 75% by weight of said slurry.

5. The slurry of claim 1 wherein said sodium bicarbonate together with said sodium chloride comprise about 70% by weight of said slurry.

6. The slurry of claim 1 wherein said slurry has a viscosity of less than about 1,000 cP.

* * * * *